United States Patent [19]

Balisky

[11] Patent Number: 4,820,278
[45] Date of Patent: Apr. 11, 1989

[54] NON-CONTAMINATING RENEWABLE SYRINGE

[75] Inventor: Todd A. Balisky, Fullerton, Calif.

[73] Assignee: The Boeing Company, Seattle, Wash.

[21] Appl. No.: 143,181

[22] Filed: Jan. 13, 1988

[51] Int. Cl.$^4$ .............................................. A61M 5/315
[52] U.S. Cl. .................................... 604/218; 604/230; 92/248
[58] Field of Search ................. 604/218, 187, 230; 92/248; 29/267

[56] References Cited

U.S. PATENT DOCUMENTS

| | | |
|---|---|---|
| 2,607,342 | 8/1952 | Abel . |
| 2,735,735 | 2/1956 | Abel . |
| 2,812,763 | 11/1957 | Ferguson . |
| 2,856,923 | 10/1958 | Roger et al. . |
| 3,811,441 | 5/1974 | Sarnoff . |
| 3,884,229 | 5/1975 | Raines et al. . |
| 3,895,633 | 7/1975 | Bartner et al. . |
| 3,941,131 | 3/1976 | Ogle . |
| 4,074,715 | 2/1978 | Geiger . |
| 4,089,335 | 5/1978 | Harris ........................ 604/230 X |
| 4,500,310 | 2/1985 | Christinger . |
| 4,501,192 | 2/1985 | Knodel ........................ 604/230 X |

Primary Examiner—John D. Yasko
Attorney, Agent, or Firm—Finnegan, Henderson, Farabow, Garrett, & Dunner

[57] ABSTRACT

A syringe which has a barrel, an annular elongate liner that is constrained by the barrel and a plunger head. The liner and the plunger head are made of a fluorinated polymer material, such as Teflon. The plunger head has first and second sealing surfaces and a portion of reduced diameter between them. The first sealing surface provides a fluid seal whereby fluid is drawn into and forced out of the syringe. The second sealing surface forms a particle trap with the inner bore of the liner to keep any fluorinated polymer particles from escaping from the portion of reduced diameter between the first and second sealing surfaces.

8 Claims, 2 Drawing Sheets

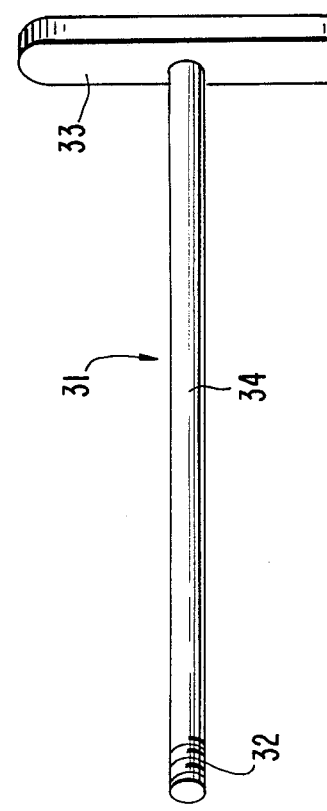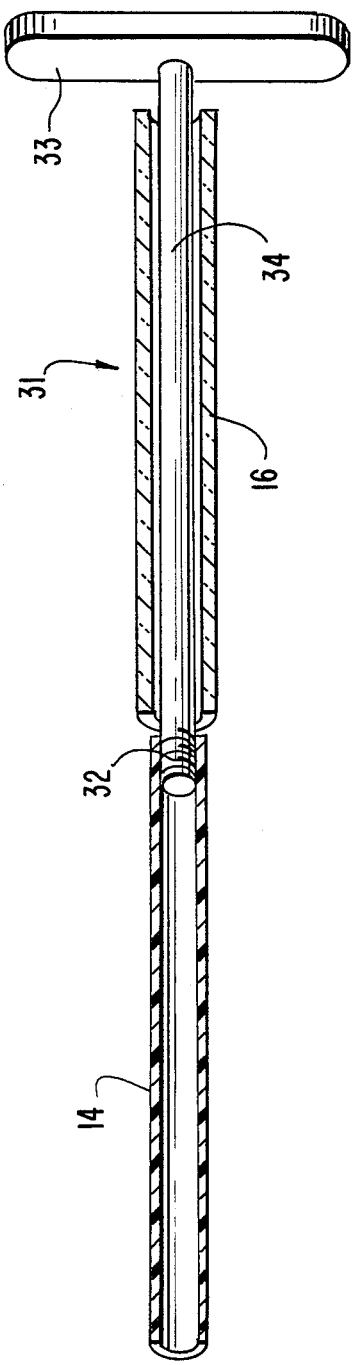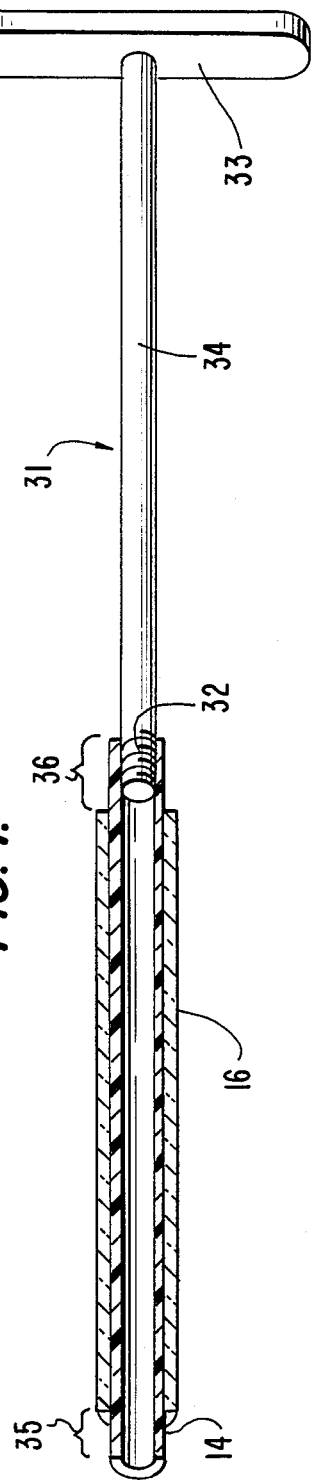

NON-CONTAMINATING RENEWABLE SYRINGE

BACKGROUND OF THE INVENTION

The present invention relates to syringes and, more particularly, to syringes which are useful in chemical-analysis applications.

In the art of chemical analysis, it is often necessary to be able to take samples of a repeatable, known volume and inject them into analytical instruments. It is further desirous to take samples with an instrument wherein the quality and volume of the sample can be viewed and which is inexpensive so as to be disposable. A conventional instrument to effect such injections is a syringe which is commonly made of plastic or glass with plastic or rubber parts. Such a syringe includes a barrel with a constriction at one end, for containing the sample fluid, and a plunger which is moveable along the inside diameter of the barrel to force the sample fluid through the constriction.

Some sample fluids to be injected consist, however, of highly corrosive liquids or other materials, such as, for example, hydrofluoric, sulfuric, nitric, or chromic acid. Few materials can withstand chemical attack by all such solutions, including glass and stainless steel. Fluorinated polymers, and in particular polymerized tetrafluorethylene resin, available under the name Teflon, a trademark of the DuPont Corporation of Wilmington, Delaware, can, however, withstand chemical attack by such chemicals.

The use of fluorinated polymers having the characteristics of Teflon in syringes presents several problems. Namely, first the cold flow of Teflon tends to cause a loss of seal between the plunger and barrel if they are made of Teflon. Second, flaking from both a plunger and a barrel made of Teflon jeopardizes the integrity of the sample and downstream equipment by contaminating the sample fluid with Teflon particles. Third, Teflon material itself is costly and is difficult to machine.

SUMMARY OF THE INVENTION

It is an object of the present invention to provide a syringe of a fluorinated polymer, such as Teflon, that is not susceptible to chemical attack.

It is another object of the present invention to provide a Teflon syringe that is constructed to overcome the adverse effects of Teflon cold flow.

It is another object of the present invention to provide a Teflon syringe that does not release Teflon particles into the sample fluid.

It is also another object of the present invention to provide a syringe which can be easily and inexpensively renewed.

It is another object of the present invention to provide a Teflon syringe wherein a contained sample is visible on external examination of the syringe.

It is a still further object of the present invention to provide a Teflon syringe that can be used with existing analytical instruments without requiring such instruments to be modified.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the syringe assembly of this invention comprises a dimensionally stable annular elongate barrel having an internal wall of a predetermined dimension; an annular elongate liner of a fluorinated polymer material disposed in the annular barrel, the liner having an external wall dimensioned for intimate physical engagement with the internal wall of the barrel, the liner having an internal wall for forming a bore of a second predetermined dimension; a plunger head of a fluorinated polymer material, having first and second axially spaced sealing surfaces disposed in the bore; the first sealing surface having a first radial dimension for slidably engaging the internal wall of the liner with a radial force sufficient to draw liquid into and force liquid out of the bore in response to axial movement of the plunger head along the bore in opposite directions; the plunger head having a portion of reduced diameter between the first and second sealing surfaces for collecting particles of any fluorinated polymer material abraded from the liner and the plunger; and the second sealing surface, having a second radial dimension less than that of the first sealing surface but sufficient for forming a particle trap with the bore so as to prevent the particles of fluorinated polymer material from passing out of the particle trap and into the solution.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 5 is a side view of a tool used to position a liner in a syringe barrel; and FIGS. 6 and 7 are sectional views of the tool of FIG. 5 being used to position a liner into a syringe barrel.

DESCRIPTION OF THE PREFERRED EMBODIMENT

Reference will now be made to the present preferred embodiment of the invention, an example of which is illustrated in the accompanying drawings.

Figure 1:
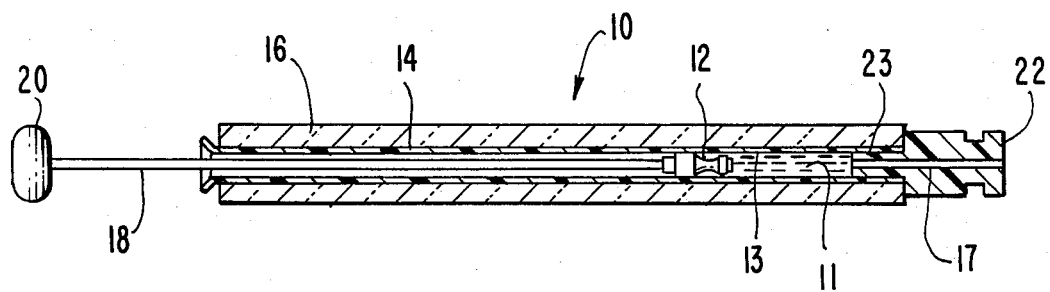
FIG. 1 is a side sectional view of a syringe assembly constructed in accordance with the present invention.

The preferred embodiment of a syringe constructed in accordance with the present invention is shown in FIG. 1 and represented generally by the numeral 10. The syringe in accordance with the invention includes a dimensionally stable, annular, elongate, preferably translucent barrel having an internal wall of a predetermined dimension. As embodied herein, this barrel 16 is circular in crosssection and has an internal wall of a predetermined dimension.

Figure 2:
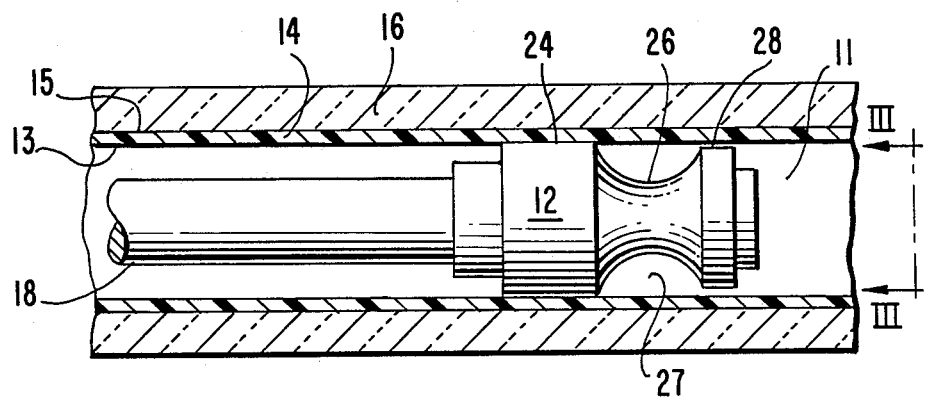
FIG. 2 is an enlarged, fragmentary view of a syringe showing in more detail the double ring plunger head and liner of the syringe assembly of FIG. 1.

In accordance with the present invention, the syringe includes an annular, elongate liner of a fluorinated polymer material disposed in the annular barrel. The liner has an external wall dimensioned for intimate physical engagement with the internal wall of the barrel; and has an internal wall that forms a bore of a second predetermined dimension. As embodied herein liner 14, as shown in FIG. 2, has a bore 13 and an external wall 15. The barrel 16 has an internal wall that is in intimate physical contact with the external wall 15 of the liner 14. Thus, the barrel 16 constrains the liner 14 by its external wall 15. An adapter 22 is provided to effect a fluid interconnection between the syringe 10 and an analytical instrument or fluid path, (not shown). The adapter 22 itself is provided with a nipple 23 which is constrained within one end of the bore 13 of the liner 14.

In accordance with the present invention, the syringe also includes a plunger head of a fluorinated polymer material, that has first and second axially spaced sealing surfaces disposed in the bore. As embodied herein and shown in FIG. 2, the plunger head 12 is slidably constrained within the bore 13 of the liner 14. Also provided is a plunger shank 18 which is connected at one end thereof to the plunger head 12 and at the other end thereof to a plunger handle 20 as shown in FIG. 1. In this way, as the handle 20 is moved in an axial direction along the liner bore 13 the plunger shank 18 is similarly caused to move which causes the plunger head 12 also to move in a direction along the liner bore 13. Thus, sample fluid contained in a sample volume 11, which is defined by the bore 13 of the liner 14, the plunger head 12 and the adapter 22, is forced out of the syringe 10, through an adapter bore 17, by the plunger head 12 being moved toward the adapter 22.

The plunger head of the syringe, in accordance with the present invention, includes a first sealing surface having a first radial dimension for slidably engaging the bore of the liner with a radial force sufficient to draw liquid into and force liquid out of the bore in response to axial movement of the plunger head along the bore in opposite directions, and a portion of reduced diameter between the first and second sealing surfaces for collecting particles of the fluorinated polymer material abraded from the liner and the plunger.

Figure 3:
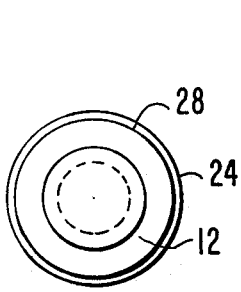
FIG. 3 is a view of the plunger head of FIG. 2 taken on the line III—III of FIG. 2.

As herein embodied, and illustrated in FIG. 2, the plunger head 12 includes a first sealing surface 24, a second sealing surface 28, and, between the first and second sealing surfaces 24 and 28, respectively, is a groove 26 which is a portion of reduced diameter. The groove 26 and the inside bore 13 of the liner 14 define a collection space or volume 27 therebetween. As illustrated in FIGS. 2 and 3, the second sealing surface 28 has a lesser diameter than the first sealing surface 24 and the groove 26 preferably has an annular shape and is of a lesser diameter than the second sealing surface 28. The second sealing surface 28 and the first sealing surface 24 are preferably cylindrically shaped sections of the plunger head 12.

The first sealing surface 24 has a radial dimension large enough so that it slidably engages the bore 13 of the liner 14. The radial force exerted by the first sealing surface 24 on the bore 13 must be sufficient to draw liquid into and force liquid out of the bore 13 as the plunger head 12 is reciprocated along the axis of the bore 13 in opposite directions. The radial dimension of the first sealing surface 24 must be small enough to prevent excessive wear of the inside bore 13 of the liner 12 yet allow easy movement of the plunger head 12 within the inside bore of the liner.

In accordance with the present invention, the syringe has a second sealing surface that has a second radial dimension that forms a particle trap with the bore to prevent the particles from passing through the particle trap.

As herein embodied the second sealing surface 28 has a diameter sufficiently large to form a particle trap between the second sealing surface 28 and the inside bore 13 of the liner 14 that prevents particles abraded from the liner 14 from passing from the collection volume 27 to the sample volume 11. In this way a filter or particle trap is defined between the first and the second sealing surfaces 24 and 28, and the bore 13 of the liner 14.

In such an embodiment, plunger head 12 affects a fluid seal between the plunger head 12 and the inside bore 13 of the liner 14 while mitigating any degradation of the inside bore 13 of the liner 14. In addition, any particles abraded from the inside bore 13 of the liner 14 or from the plunger head 12 will be trapped in the collection volume 27, since any clearance between the outside diameter of the second sealing surface 28 and the inside bore 13 of the liner 14 is sufficiently small to prevent the passage of particles entrapped in the collection volume 27.

Figure 4:
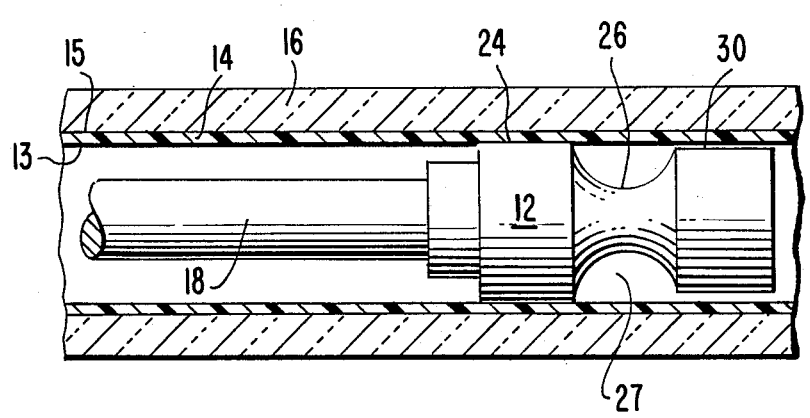
FIG. 4 is a fragmentary view of the syringe assembly of FIG. 2 having a modified plunger head.

Although enlarged FIGS. 2 and 4 depict a clearance between the second sealing surface 28 and the bore for clarity of illustration, it has been found that the second sealing surface 28 may have an interference fit of 0.002 inches to a clearance of 0.002 inches to act as a particle trap. The first sealing surface 24 may have an interference fit of 0.003 to 0.005 inches to provide a fluid seal without undersired abrasion of the inside bore 13 of the liner 14. The foregoing dimensions have been found to be effective in accomplishing the objects of the present invention when the bore 13 of the liner 14 has a diameter of 0.190 inches.

It has further been found that the relative axial lengths of the first sealing surface 24 and the second sealing surface 28 are not critical to accomplish the purposes and objectives of the present invention. Accordingly, the axial length of the first sealing surface 24 may be greater than that of the second sealing surface 28, as illustrated in FIG. 2. A modified plunger head 12 is shown in FIG. 4 wherein a second sealing surface 30 is provided having an axial length equal to that of the axial length of the first sealing surface 24.

Preferably, the liner 14 is made of a fluorinated polymer such as polymerized tetrafluoroethelene resin which is available under the trademark Teflon from the DuPont Corporation of Wilmington, Delaware. Such materials are not subject to chemical attack by acids such as hydrofluoric, sulfuric, nitric or chromic. Accordingly, when exposed to such chemicals the chemical integrity of the liner is maintained.

It is also preferred that the liner 14 be fixedly constrained by a barrel 16. The barrel 16 can be, for example, made of glass. In this way a liner made of materials which are subject to cold flow can be held in a constant desired shape so as to maintain the seal affected between the plunger head 12 and the inside bore of the liner 14. Further, if the barrel is made of a translucent material, such as glass, and the liner 14 is also made of a translucent material, such as Teflon, the presence of a sample as well as its color and quantity can be viewed from outside the syringe 10.

The liner 14 can be of any cross-sectional shape; that is, circular, triangular, oval, rectangular or any variations thereof, provided the plunger head 12 and the interior of barrel 16 and liner 14 have a corresponding shape and clearance.

The liner 14 is positioned in the barrel 16 by means of a hand tool 31, shown in FIG. 5. The hand tool 31 includes a shaft 34, the shaft 34 having a threaded tip 32 at one end and a handle 33 at the other end thereof. The size of the threaded tip 32 is chosen so that it will engage the liner 14 when turned into it and release the liner 14 easily when turned out of the liner 14. Typically, this thread size is chosen to be midway between the outside and inside diameter of the liner 14.

FIGS. 6 and 7 illustrate how the tool 31 shown in FIG. 5 is used to insert a liner 14 into a syringe barrel 16. To insert liner 14 into the syringe barrel 16, hand tool 31 is slid through an empty barrel 16 until the tool tip 32 comes out the other end. Liner 14 is then rotated onto the tool tip 32, and the liner 14 is positioned into the barrel 16 by pulling on handle 33 until liner 14 appears at both ends of barrel 16. Excess liner ends, such as liner ends 34 and 36, may then be trimmed off of each end of the barrel 16 through any convenient means. Liner 14 is removed in a similar manner by turning the tool tip 32 into either end of the liner 14 and pulling on handle 33 until liner 14 is removed from the barrel 16.

It will be apparent to those skilled in the art that various modifications and variations can be made in the syringe of the present invention and in the construction of its plunger head without departing from the scope or spirit of the invention. Thus, it is intended that the present invention cover the modifications and variations of this invention provided they come within the scope of the appended claims and their equivalents.

What is claimed is:

1. A syringe comprising:
   a dimensionally stable, annular, elongate barrel having an internal wall of a predetermined dimension;
   an annular, elongate liner of a fluorinated polymer material disposed in said annular barrel, said liner having an external wall dimensioned for intimate physical engagement with said internal wall of said barrel, said liner having an internal wall forming a bore of a second predetermined dimension;
   a plunger head of a fluorinated polymer material, having first and second axially spaced sealing surfaces disposed in said bore;
   said first sealing surface having a first radial dimension for slidably engaging said bore of said liner with a radial force sufficient to draw liquid into and force liquid out of said bore in response to axial movement of the plunger head along said bore in opposite directions;
   said plunger head having a portion of reduced diameter between said first and second sealing surfaces for collecting particles of said fluorinated polymer material abraded from said liner and said plunger; and
   said second sealing surface, having a second radial dimension, forming a particle trap with said bore to prevent said particles from passing through the particle trap.

2. A syringe as claimed in claim 1 wherein said barrel and and said liner are substantially translucent for visually determining the presence and level of fluid in said bore of said liner.

3. A syringe as claimed in claim 1 wherein said liner and said plunger head are made of a Teflon resin.

4. A syringe as claimed in claim 1 wherein said first radial dimension is on the order of 0.003–0.005 inch larger than the inside diameter of said bore and the second radial dimension is on the order of 0.002 inch smaller to 0.002 inch larger than the inside diameter of said bore.

5. A syringe as claimed in claim 3 wherein the inside diameter of said bore is 0.190 inch.

6. A syringe as claimed in claim 1 wherein the axial length of said first and second sealing surfaces is substantially equal.

7. A syringe as claimed in claim 1 wherein the axial length of said first sealing surface is greater than the axial length of said second sealing surface.

8. A tool for inserting a liner into a syringe barrel having an internal wall of a pre-determined dimension where the liner has an external wall dimensioned for intimate physical engagement with the internal wall of the barrel comprising:
   a shaft having an outside diameter smaller than the diameter of the internal wall of the syringe barrel, a first end, and a second end;
   handle means disposed at said first end of said shaft for reciprocably moving said shaft; and
   engagement means at said second end of said shaft for removably engaging the liner.

* * * * *